(12) United States Patent
Takeuchi et al.

(10) Patent No.: US 7,800,656 B2
(45) Date of Patent: Sep. 21, 2010

(54) ENDOSCOPE APPARATUS

(75) Inventors: Shinji Takeuchi, Saitama (JP); Kazunori Abe, Saitama (JP); Daisuke Ayame, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 1253 days.

(21) Appl. No.: 11/356,033

(22) Filed: Feb. 17, 2006

(65) Prior Publication Data

US 2006/0197831 A1 Sep. 7, 2006

(30) Foreign Application Priority Data

Mar. 4, 2005 (JP) .......................... P. 2005-060199

(51) Int. Cl.
*H04N 13/00* (2006.01)
*H04N 5/228* (2006.01)
(52) U.S. Cl. .................. 348/222.1; 348/45; 348/65; 348/231.6
(58) Field of Classification Search ............ 348/207.99, 348/222.1, 45, 65–72, 231.1, 231.6; 600/109, 600/118
See application file for complete search history.

(56) References Cited

U.S. PATENT DOCUMENTS

| | | | |
|---|---|---|---|
| 4,860,095 A | 8/1989 | Kimura et al. | |
| 4,885,634 A | 12/1989 | Yabe | |
| 5,408,263 A * | 4/1995 | Kikuchi et al. | 348/68 |
| 6,943,822 B2 * | 9/2005 | Iida et al. | 348/65 |
| 7,204,803 B2 * | 4/2007 | Ueno et al. | 600/109 |
| 2003/0001952 A1 | 1/2003 | Iida et al. | |
| 2003/0179291 A1 | 9/2003 | Kobayashi et al. | |
| 2004/0141054 A1 | 7/2004 | Mochida et al. | |

FOREIGN PATENT DOCUMENTS

| | | |
|---|---|---|
| EP | 1 302 152 A1 | 4/2003 |
| JP | 2002-369798 | 12/2002 |
| JP | 2003-93336 A | 4/2003 |

OTHER PUBLICATIONS

Japanese Office Action-Notification of Reason for Refusal, May 19, 2010.

* cited by examiner

*Primary Examiner*—Tuan Ho
(74) *Attorney, Agent, or Firm*—Birch, Stewart, Kolasch & Birch, LLP

(57) ABSTRACT

An endoscope apparatus comprises: an endoscope comprising an imaging device that forms color image signals of a body to be observed; a Y/C signal processing circuit that forms brightness/color difference signals from a color image signal obtained by the imaging device; a storage portion that stores Y/C matrix data for forming a spectral image based on the brightness/color difference signals; and a Y/C spectral image forming circuit that conducts matrix calculation by the Y/C matrix data of the storage portion and the brightness/color difference signals output from the Y/C signal processing circuit and forms a spectral image of an arbitrarily selected wavelength range.

3 Claims, 3 Drawing Sheets

ENDOSCOPE APPARATUS

This Nonprovisional application claims priority under 35 U.S.C. §119(a) on Patent Application No(s). JP 2005-060199 filed in Japan on Mar. 4, 2005, the entire contents of which is hereby incorporated by reference.

BACKGROUND OF THE INVENTION

1. Field of the Invention

The present invention relates to an endoscope apparatus, more particularly, a constitution used in medical fields for forming and displaying a spectral image (video) made up of image information of arbitrarily selected wavelength ranges.

2. Description of the Related Art

Recently, in a electronic endoscope apparatus which uses a solid imaging device, spectral imaging combined with a narrow band pass filter on the basis of a spectral reflectance in alimentary canal (gastric mucosa and the like), namely, a narrow band filter built-in an electronic endoscope apparatus (Narrow Band Imaging-NBI) has become the focus of attention. In place of rotational filters of R (red), G (green) and B (blue) by a frame sequential method, this system is provided with band pass filters of three narrow bands (wavelengths), outputs sequentially illumination light via these narrow band-pass filters, and conducts processing the same as in the case of red (R), green (G) and blue (B) signals while changing respective weightings to three signals obtained from these illumination lights, thereby forming a spectral image. This spectral image is able to realize micro-structures and the like in gastrointestinal tracts such as the stomach and large intestine, which would otherwise not be realized.

In contrast, unlike the frame sequential method using the above-described narrow band pass filters, as described in Japanese Published Unexamined Patent Application No. 2003-93336, it has been proposed that in the simultaneous method in which micro-mosaic color filters are arranged on a solid imaging device, a spectral image is formed by the computing process on the basis of image signals obtained from white light. In this method, the relationship between numeric data of the respective R, G, and B color sensitivity characteristics and numeric data of spectral characteristics of a specific narrow bandpass is determined as matrix data (coefficient sets) and computing is made for the matrix data and the R, G and B signals to obtain spectral image signals artificially via the narrow bandpass filters. Where a spectral image is formed by such computing, it is not necessary to provide a plurality of filters corresponding to desired wavelength ranges and to provide these change-over arrangements, thereby successfully avoiding increases in the size of a system and reducing cost.

However, in forming a spectral image by the endoscope apparatus, underlying color image signals are R (red), G (green) and B (blue) signals. When a solid imaging device is used, for example, a complementary color-type CCD having color filters Mg, Ye, Cy and G, Mg (magenta), Ye (yellow), Cy (cyan), and G (green) signals are often converted to a brightness (Y) signal and a color difference (C) signal (Y/C signals) for processing. Also, the Y/C signals must be subjected to color conversion to RGB signals. Further, where an elementary color-type CCD having RGB color filters is used, RGB signals are converted to Y/C signals due to matters related to a variety of signal processings and circuit configurations at subsequent steps. In this case, it is necessary to make RGB signals from Y/C signals. Such color conversion processings are in principle redundant, and such a problem is brought about whereby repeated color conversion may cause deterioration in quality of images and complicate the circuit configuration.

On the other hand, recently, endoscope apparatuses in which different types of endoscopes (scope) are connected to a single endoscope have been used. In this case, Y/C signals or RGB signals are outputted from the endoscope, and a spectral image may not be formed depending on output formats of the endoscope. Therefore, user-friendly endoscope apparatuses have been demanded in view of such circumstances.

SUMMARY OF THE INVENTION

The present invention has been made in view of the above problem, and an object of the invention is to provide a user-friendly endoscope apparatus capable of forming a spectral image directly from Y/C signals and also obtaining a spectral image from either Y/C signals or RGB signals.

In order to attain the above object, an endoscope apparatus according to the first aspect of the invention comprises an endoscope comprising an imaging device that forms color image signals of a body to be observed; a Y/C signal processing circuit that forms brightness/color difference signals from a color image signal obtained by the imaging device; a first storage portion that stores Y/C matrix data for forming a spectral image based on the brightness/color difference signals; and a Y/C spectral image forming circuit that conducts matrix calculation by the Y/C matrix data of the storage portion and the brightness/color difference signals output from the Y/C signal processing circuit and forms a spectral image of an arbitrarily selected wavelength range.

An endoscope apparatus according to the second aspect of the invention comprises: an endoscope comprising an imaging device that forms color image signals of a body to be observed; an image signal processing circuit comprising one of (i) a Y/C signal processing circuit that forms brightness/color difference signals from a color image signal obtained from the imaging device and (ii) an RGB signal processing circuit that forms RGB signals from a color image signal obtained from the imaging device; a first storage portion that stores Y/C matrix data for forming a spectral image based on the brightness/color difference signals; a Y/C spectral image forming circuit that conducts matrix calculation by the Y/C matrix data of the storage portion and the brightness/color difference signals output from the Y/C signal processing circuit and forms a spectral image of a first arbitrarily selected wavelength range; a second storage portion that stores RGB matrix data for forming a spectral image based on the RGB signals (the first and second storage portions may be the same or different); and an RGB spectral image forming circuit that conducts matrix calculation by the RGB matrix data of the storage portion and the RGB signals output from the RGB signal processing circuit and forms a spectral image of a second arbitrarily selected wavelength range, wherein either the Y/C spectral image forming circuit or the RGB spectral image forming circuit can be selected.

An endoscope apparatus according to the third aspect of the invention comprises a processor unit detachably connected to the endoscope on the second aspect of the invention, wherein the image signal processing circuit is disposed in the endoscope, both of the Y/C spectral image forming circuit and the RGB spectral image forming circuit are disposed in the processor unit, and in the processor unit, either the Y/C spectral image forming circuit or the RGB spectral image forming circuit is selected based on an identification information on the endoscope.

In the above constitution according to the first aspect of the invention, since the relationship (conversion coefficient) between the Y/C signals of brightness (Y)/color difference (R−Y and B−Y) and the RGB signals has been conventionally known, matrix coefficients for computing λ1, λ2 and λ3 signals of the selected wavelength range from the Y/C signals have been previously determined on the basis of the relationship mentioned above and the relationship (conversion coefficient) between the λ1, λ2 and λ3 signals of the selected wavelength range and the RGB signals. The matrix data (coefficient sets) is stored in a computing memory on the processor unit. Then, when an operator selects three-wavelength ranges (narrow band) (one wavelength range may be selected) for forming a spectral image, matrix data corresponding to the three-wavelength ranges is read from the memory. Then, λ1, λ2 and λ3 signals are formed by the matrix data and the Y/C signals output from the DSP and others, thereby making it possible to display on a monitor the spectral image in combination with the three-wavelength ranges selected.

Further, in the above constitutions according to the second and third aspects of the invention, the processor unit connected to the endoscope can include both the Y/C spectral image forming circuit and the RGB spectral image forming circuit. Where, for example, the endoscope connected thereto outputs Y/C signals or RGB signals, spectral images respectively corresponding thereto can be formed. In addition, there is a case where the Y/C signals and the RGB signals are formed during signal processing in a single processor unit. In this case, it is possible to form a spectral image from both of these signals, whenever appropriate.

DETAILED DESCRIPTION OF THE INVENTION

Figure 1:
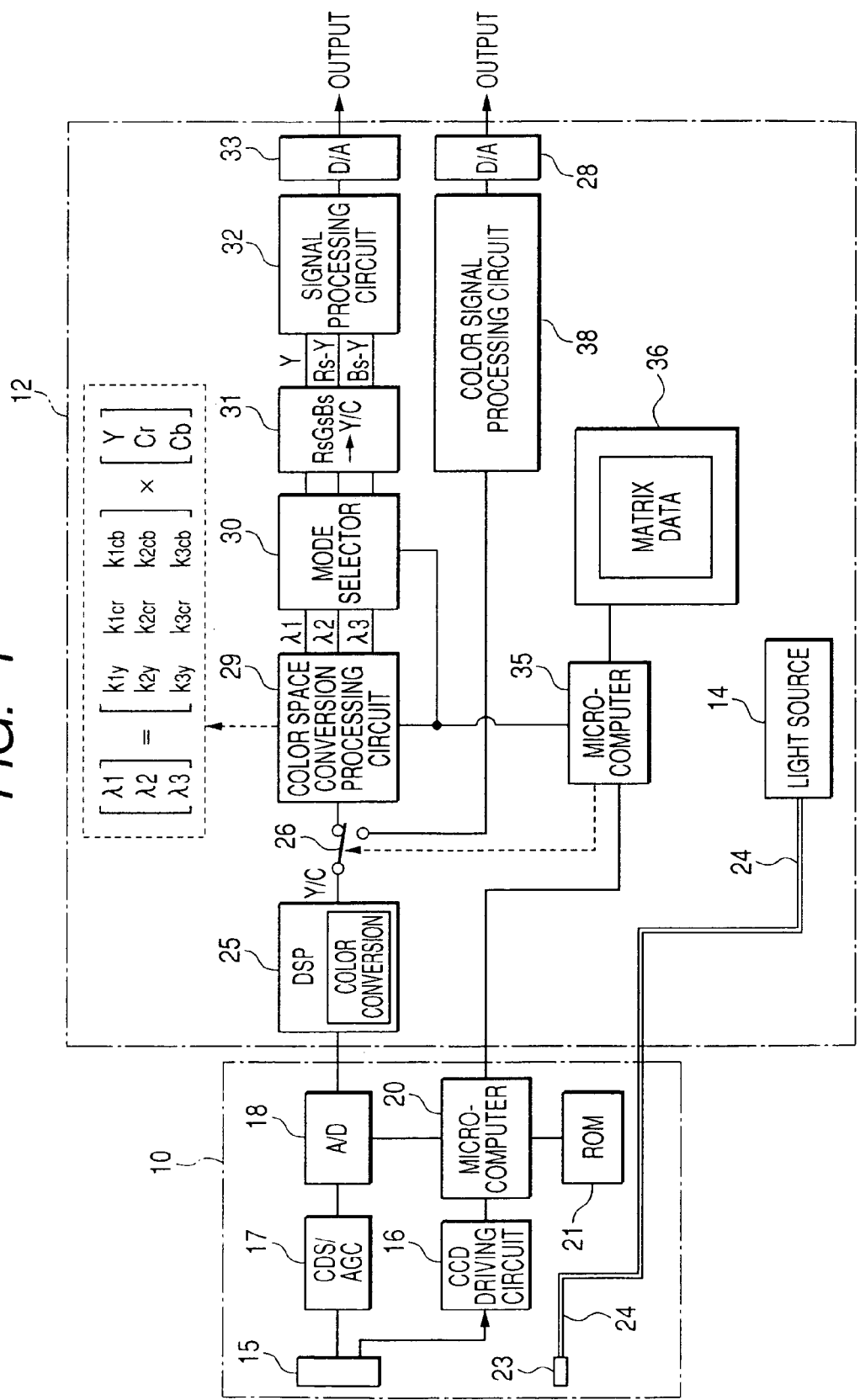
FIG. 1 is a block diagram showing the constitution of the endoscope apparatus according to the embodiment 1 of the present invention.

FIG. 1 shows a constitution of the electronic endoscope apparatus of the embodiment 1. As shown in FIG. 1, the electronic endoscope apparatus is constituted so that a scope (electronic endoscope) 10 is connected to a processor unit 12 in a freely attachable and detachable way and a light source 14 is arranged on the processor unit 12. Further, there is a case where the light source 14 is arranged on a light source unit, which is a separate body. The scope 10 is provided on the end with a CCD 15 which is a solid imaging device, and a complementary color-type CCD having, for example, color filters of Mg, Ye and Cy are used as the CCD 15 on an imaging surface.

The CCD 15 is provided with a CCD driving circuit 16 for forming a driving pulse on the basis of synchronizing signals, a CDS/AGC (correlated dual sampling/automatic gain control) circuit 17 for sampling and amplifying an image (video) signal input from the CCD 15 the image signal and an A/D converter 18. Also provided are a microcomputer 20 and a memory (ROM) 21 for controlling various circuits inside the scope 10 and also controlling communications with the processor unit 12. Identification information on the type of color filters of the CCD 15 (complementary color-type CCD or elementary color-type CCD) and the signal output mode is stored in the memory 21. Further, the scope 10 is provided at the end with an illumination window 23, and the illumination window 23 is connected to the light source 14 by a light guide 24.

The processor unit 12 is provided with a DSP (digital signal processor) 25 (corresponding to the Y/C signal processing circuit) which imparts a variety of image processings to digitally converted image signals. In the DSP 25, Y/C signals constituted by a brightness (Y) signal and a color difference [C(R−Y,B−Y)] signal are formed and output from output signals (Mg, Ye, Cy and G signals) of the CCD 15. The DSP 25 is provided with a color space conversion processing circuit 29 (corresponding to the Y/C spectral image forming circuit) for conducting matrix calculation for a spectral image via the selector 26 (other terminal). The spectral image signals of selected wavelength ranges of λ1, λ2 and λ3 are output from a color space conversion processing circuit 29. At the post-stage of the color space conversion processing circuit 29, a mode selector 30 for selecting either the spectral image (monochrome mode) made up of one wavelength range (narrow band) or the spectral image (three-color mode) made up of three wavelength ranges (the mode selector may be provided with a two color mode by which two colors are selected), a color conversion circuit 31 for inputting image signals (λ1, λ2 and λ3) made up of one wavelength range or three wavelength ranges as Rs, Gs and Bs signals in order to conduct a processing which corresponds to conventional RGB signals and for converting these Rs, Gs and Bs signals to Y/C signals, and a signal processing circuit 32 for conducting a variety of other signal processing (mirror image process, mask generation, character generation and the like), and a D/A converter 33. Further, the DSP 25 may be arranged on the scope 10.

A microcomputer 35 is also provided which communicates with the scope 10 and also controls various circuits inside the processor unit 12, reading matrix data from a memory 36 (corresponding to the first storage portion) to supply the data to the color space conversion processing circuit 29. Matrix (coefficient) data table) for forming a spectral image on the basis of Y/C signals are stored in the memory 36. According to the embodiment, table 1 below shows one example of the matrix data accommodated in the memory 36.

TABLE 1

| Parameter | $k_{py}$ | $k_{pcr}$ | $k_{pcb}$ |
|---|---|---|---|
| p1 | 0.000008 | −0.0002 | 0.000802 |
| . | . | . | . |
| . | . | . | . |
| . | . | . | . |
| p18 | 0.00241 | 0.006147 | −0.00289 |
| p19 | 0.00603 | 0.005843 | −0.00294 |
| p20 | 0.001037 | 0.005427 | −0.00294 |
| p21 | 0.001549 | 0.004912 | −0.00288 |
| p22 | 0.002132 | 0.004283 | −0.00277 |
| p23 | 0.002767 | 0.003563 | −0.00263 |
| . | . | . | . |
| . | . | . | . |
| . | . | . | . |
| p43 | 0.00708 | −0.00139 | −0.00149 |
| p44 | 0.007294 | −0.00165 | −0.0014 |
| p45 | 0.007484 | −0.00188 | −0.00132 |
| p46 | 0.007638 | −0.00206 | −0.00124 |
| p47 | 0.007732 | −0.00219 | −0.00116 |
| p48 | 0.007792 | −0.00228 | −0.00108 |

TABLE 1-continued

| Parameter | $k_{py}$ | $k_{pcr}$ | $k_{pcb}$ |
|---|---|---|---|
| p49 | 0.007834 | −0.00234 | −0.00102 |
| p50 | 0.007864 | −0.00237 | −0.00098 |
| p51 | 0.007903 | −0.00238 | −0.00097 |
| p52 | 0.007956 | −0.00238 | −0.00097 |
| . | . | . | . |
| . | . | . | . |
| . | . | . | . |
| p61 | 0.008051 | −0.00216 | −0.00094 |

Matrix data shown in the above Table 1 is made up of 61-wavelength range parameters (coefficient sets) p1 to p61 in which, for example, the wavelength range from 400 nm to 700 nm is divided at 5 nm intervals. The parameters p1-p61 are constituted by coefficients, $k_{py}$, $k_{pcr}$ and $k_{pcb}$ (p corresponds to p1-p61) for matrix calculation.

Then, in the color space conversion processing circuit 29, matrix calculation is conducted according to the following mathematical formula 1 represented by the coefficients $k_{py}$, $k_{pcr}$ and $k_{pcb}$, and Y/C signals (R−Y=Cr and B−Y=Cb) output from the DSP 25.

$$\begin{bmatrix} \lambda 1 \\ \lambda 2 \\ \lambda 3 \end{bmatrix} = \begin{bmatrix} k1y & k1cr & k1cb \\ k2y & k2cr & k2cb \\ k3y & k3cr & k3cb \end{bmatrix} \times \begin{bmatrix} y \\ Cr \\ Cb \end{bmatrix}$$ [Mathematical Formula 1]

More specifically, where, for example, the parameter p21 (center wavelength 500 nm), p45 (center wavelength 620 nm) and p51 (center wavelength 650 nm) shown in Table 1 are selected as λ1, λ2 and λ3, (−0.001549, 0.004912, −0.00288) of p21, (0.007484, −0.00188, −0.00132) of p45 and (0.007903, −0.00238, −0.00097) of p51 may be substituted as coefficients ($k_{py}$, $k_{pcr}$ and $k_{pcb}$).

Further, a color signal processing circuit 38 for forming ordinary color images (videos) not for spectral images and a D/A converter 39 are connected and arranged on the other terminal of the selector 26.

The embodiment 1 is constituted as described above. In the scope 10 shown in FIG. 1, the CCD driving circuit 16 drives the CCD 15, by which imaging signals of a body to be observed are output from the CCD 15. The signals are subjected to the correlated dual sampling and amplification at the CDS/AGC circuit 17, and then supplied via the A/D converter 18 to the DSP 25 of the processor unit 12 as a digital signal. In the DSP 25, gamma processing is given to output signals from the scope 10 and also color conversion processing is given to signals obtained via color filters of Mg, Ye, Cy and G, thereby forming Y/C signals made up of a brightness (Y) signal and a color difference (R−Y,B−Y) signal. Output of the DSP 25 is usually supplied to the color signal processing circuit 38 by the selector 26. The output is subjected to the signal processing similar to the conventional processing and supplied via the D/A converter 39 to a monitor and color images of an ordinary body to be observed are displayed on the monitor.

Upon depression of an operating switch arranged on an operation portion and others for forming spectral images, the selector 26 changes Y/C signals output from the DSP 25 so as to supply them to a color space conversion processing circuit 29. At this time, an operator selects three wavelength ranges corresponding to signals of λ1, λ2 and λ3, and the microcomputer 35 reads matrix (coefficient) data corresponding to three selected wavelength ranges from the memory 36 (Table 1) and supplies the data to a color space conversion processing circuit 29.

In the color space conversion processing circuit 29, in order to form spectral images, matrix calculation is conducted according to the above mathematical formula 1. Where p21 (center wavelength 500 nm), p45 (center wavelength 620 nm) and p51 (center wavelength 652 nm) are selected, for example, as three wavelength ranges (λ1, λ2 and λ3), signals λ1, λ2 and λ3 are determined by matrix calculation according to the following mathematical formula 2 represented by RGB signals.

$$\begin{bmatrix} \lambda 1 \\ \lambda 2 \\ \lambda 3 \end{bmatrix} = \begin{bmatrix} -0.001549 & 0.004912 & -0.00288 \\ 0.007484 & -0.00188 & -0.00132 \\ 0.007903 & -0.00238 & -0.00097 \end{bmatrix} \times \begin{bmatrix} Y \\ Cr \\ Cb \end{bmatrix}$$ [Mathematical formula 2]

Then, where a three-color mode is selected by the mode selector 30, the above signals of λ1, λ2 and λ3 are supplied to the color conversion circuit 31 as signals of Rs (=λ1), Gs (=λ2) and Bs (=λ3). Where a monochrome mode is selected, any one of the above signals of λ1, λ2 and λ3 is supplied to the color conversion circuit 31 as the signal of Rs (=λ2), Gs (=λ2) or Bs (=λ2) (for example, λ2 is selected). In the color conversion circuit 31, signals of λ1, λ2 and λ3 as Rs, Gs and Bs signals are converted to Y/C signals (Y, Rs−Y and Bs−Y), and the Y/C signals are supplied to a monitor and others via the signal processing circuit 32 and the D/A converter 33.

Figure 2:
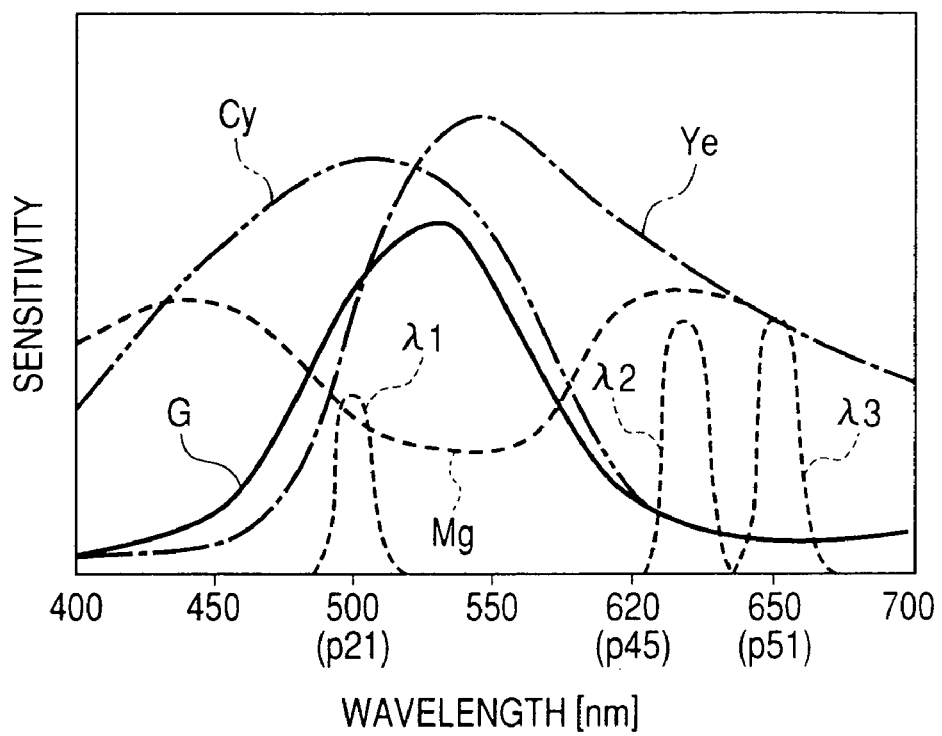
FIG. 2 is a graph showing one example of the wavelength range of spectral images formed in the embodiment 1, together with the spectral sensitivity characteristics of the complementary color-type CCD.
Figure 3:
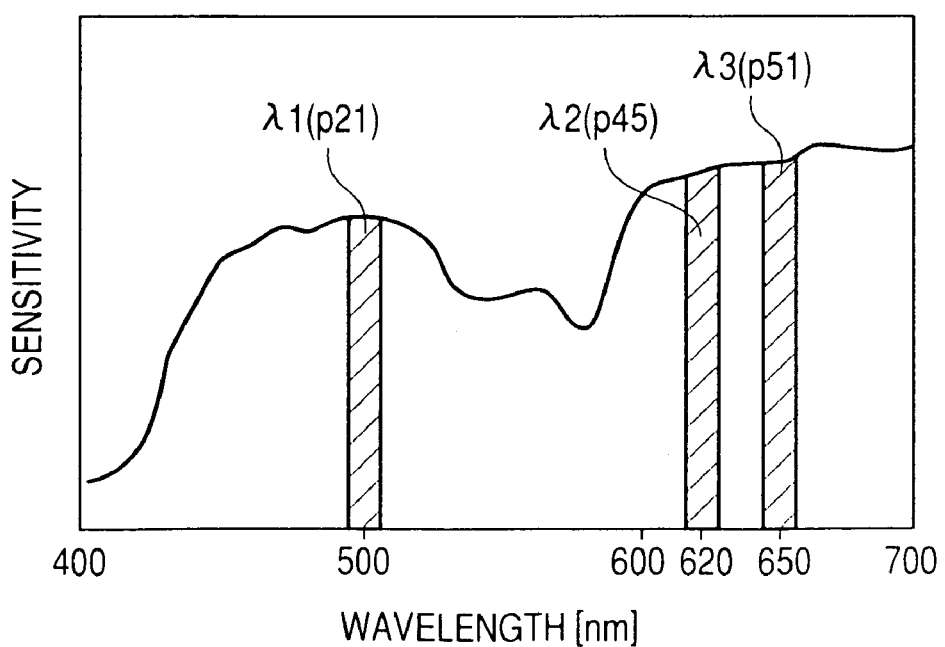
FIG. 3 is a graph showing one example of the wavelength range of spectral images formed in the embodiment 1, together with the reflection spectrum of a living body.

As described above, spectral images displayed on a monitor and others are constituted by color components of the wavelength ranges shown in FIG. 2 and FIG. 3. More specifically, FIG. 2 is a conceptual diagram in which three wavelength ranges forming spectral images are superimposed on the spectral sensitivity characteristics of color filters on the CCD 15 (complementary color-type CCD) (the color filter is not in agreement with the sensitivity graduation of wavelength ranges corresponding to λ1, λ2 and λ3 signals). Further, FIG. 3 is a conceptual diagram in which three wavelength ranges are superimposed on the reflection spectrum of a living body. The wavelengths of p21, p45 and p51 selected as λ1, λ2 and λ3 signals in the embodiment 1 are color signals having the wavelength range of approximately ±10 nm, with the center wavelength being 500 nm, 620 nm and 650 nm in sequence, as illustrated in the diagram. Displayed are spectral images (moving image and still image) constituted by a combinations of colors of the three wavelength ranges.

Next, a description is given for case in which the above matrix coefficient data (Y/C matrix data) shown in Table 1 can be determined from the matrix coefficients (RGB matrix data) where spectral images are formed by matrix calculation for RGB signals. More specifically, in general, the relationships between the RGB signals and the Y/C signals are expressed by the following mathematical formulae 3 and 4.

$$\begin{bmatrix} R \\ G \\ B \end{bmatrix} = \begin{bmatrix} Ry & Rr & Rb \\ Gy & Gr & Gb \\ By & Br & Bb \end{bmatrix} \times \begin{bmatrix} Y \\ Cr \\ Cb \end{bmatrix} \left( \begin{bmatrix} Ry & Rr & Rb \\ Gy & Gr & Gb \\ By & Br & Bb \end{bmatrix} = \begin{bmatrix} 1.164 & 0 & 1.596 \\ 1.164 & -0.391 & -0.813 \\ 1.164 & 2.018 & 0 \end{bmatrix} \right)$$ [Mathematical Formula 3]

$$\begin{bmatrix} Y \\ Cr \\ Cb \end{bmatrix} = \begin{bmatrix} Yr & Yg & Yb \\ Crr & Crg & Crb \\ Cbr & Cbg & Cbb \end{bmatrix} \times \begin{bmatrix} R \\ G \\ B \end{bmatrix} \left( \begin{bmatrix} Yr & Yg & Yb \\ Crr & Crg & Crb \\ Cbr & Cbg & Cbb \end{bmatrix} = \begin{bmatrix} .257 & .501 & .098 \\ -.148 & -.291 & .439 \\ .439 & -.368 & -.071 \end{bmatrix} \right)$$ [Mathematical Formula 4]

Then, when consideration is given to signals of λ1, λ2 and λ3 of narrow band image (NBI), matrix calculation based on RGB signals is represented by the following mathematical formula 5, and between the Y/C signals and λ1, λ2 and λ3 signals, the following mathematical formula 6 is established.

$$\begin{bmatrix} \lambda 1 \\ \lambda 2 \\ \lambda 3 \end{bmatrix} = \begin{bmatrix} k1r & k1g & k1b \\ k2r & k2g & k2b \\ k3r & k3g & k3b \end{bmatrix} \times \begin{bmatrix} R \\ G \\ B \end{bmatrix}$$ [Mathematical Formula 5]

$$\begin{bmatrix} Y \\ Cr \\ Cb \end{bmatrix} = \begin{bmatrix} Yr & Yg, & Yb \\ Crr & Crg & Crb \\ Cbr & Cbg & Cbb \end{bmatrix} \times \begin{bmatrix} \lambda 1 \\ \lambda 2 \\ \lambda 3 \end{bmatrix}$$ [Mathematical Formula 6]

The above mathematical formulae 5 and 6 are summarized to give the following mathematical formula 7.

$$\begin{bmatrix} Y \\ Cr \\ Cb \end{bmatrix} = \begin{bmatrix} Yr & Yg & Yb \\ Crr & Crg & Crb \\ Cbr & Cbg & Cbb \end{bmatrix} \times \begin{bmatrix} k1r & k1g & k1b \\ k2r & k2g & k2b \\ k3r & k3g & k3b \end{bmatrix} \times \begin{bmatrix} R \\ G \\ B \end{bmatrix}$$ [Mathematical Formula 7]

Therefore, as is apparent from the mathematical formula 7, the matrix coefficients shown in Table 1 according to the embodiment are determined by RGB matrix data (data of Table 2 to be explained later) and coefficients of the mathematical formula 4.

Figure 4:
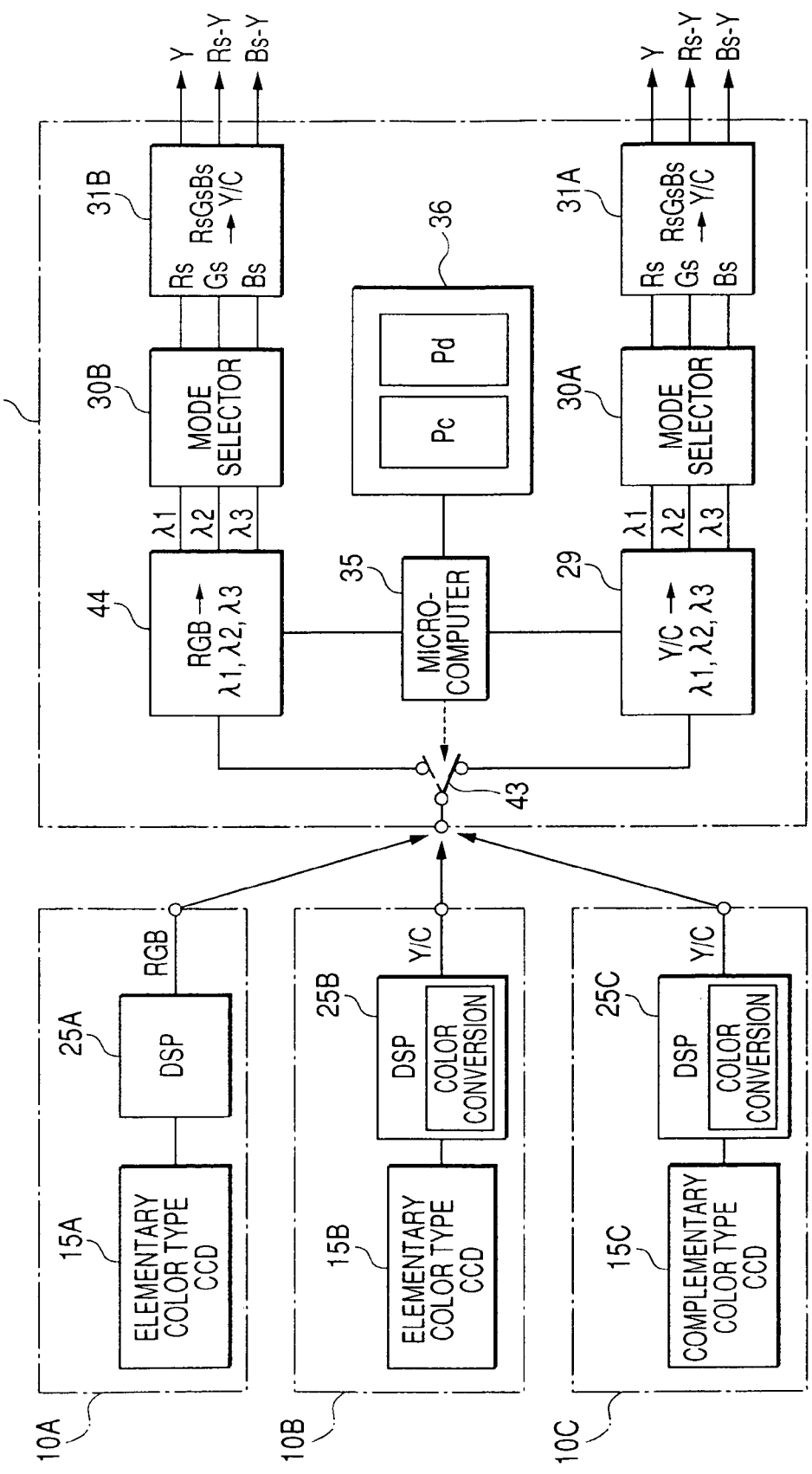
FIG. 4 is a block diagram showing the constitution of the endoscope apparatus in the embodiment 2.

FIG. 4 shows the constitution of the endoscope apparatus according to the embodiment 2, which is designed so that a spectral image can be formed by both Y/C signals and RGB signals. As shown in FIG. 4, the endoscope apparatus according to the embodiment 2 is provided with, for example, a scope 10A having an elementary color-type CCD 15A with RGB color filters and DSP 25A (corresponding to the RGB signal processing circuit) which outputs RGB signals as a color image signal, a scope 10B having an elementary color-type CCD 15B and DSP 25B (corresponding to the Y/C signal processing circuit) which converts RGB signals through color conversion processing to Y/C signals for output, and a scope 10C having a complementary color-type CCD 15C with Mg, Ye, Cy and G color filters and DSP 25C (corresponding to the Y/C signal processing circuit) which converts Mg, Ye, Cy and G signals through the color conversion processing to Y/C signals for output.

The processor 42 is provided with a color space conversion processing circuit 29 (corresponding to the Y/C spectral image forming circuit) for conducting matrix calculation for Y/C signals via the selector 43 as with the embodiment 1, a mode selector 30A and a color conversion circuit 31A for converting Rs, Gs and Bs signals to which λ1, λ2 and λ3 signals are substituted, as they are, to Y/C signals as a Y/C spectral image forming circuit. It is also provided with a color space conversion processing circuit 44 (corresponding to the RGB spectral image forming circuit) for conducting matrix calculation for RGB signals as an RGB spectral image forming circuit, a mode selector 30B and a color conversion circuit 31B for converting Rs, Gs and Bs signals (λ1, λ2 and λ3 signals) to Y/C signals. Further, the Y/C matrix data Pc shown in the above Table 1 and the RGB matrix data Pd shown in the following Table 2 are stored in the memory 36 (corresponding to the first and second storage portions) which is connected to the microcomputer 35.

TABLE 2

| Parameter | $k_{pr}$ | $k_{pg}$ | $k_{pb}$ |
|---|---|---|---|
| p1 | 0.000083 | −0.00188 | 0.003592 |
| . | . | . | . |
| . | . | . | . |
| . | . | . | . |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −3.6E−05 |
| p51 | 0.005152 | −0.00192 | 0.000088 |
| p52 | 0.005215 | −0.00207 | 0.000217 |
| . | . | . | . |
| . | . | . | . |
| p61 | 0.00548 | −0.00229 | 0.00453 |

As with the matrix data Pc shown in Table 1, the matrix data Pd in Table 2 is also data in which the wavelength range from 400 nm to 700 nm is divided into 61 wavelength range parameters (coefficient sets) p1 to p61 and constituted by the matrix coefficients $k_{pr}$, $k_{pg}$ and $k_{pb}$ corresponding to these parameters p1 to p61. In the color space conversion processing circuit 44, matrix calculation is conducted according to the above mathematical formula 5 represented by the coefficients $k_{pr}$, $k_{pg}$ and $k_{pb}$ and RGB signals input from the endoscope 10A, thereby forming a spectral image.

More specifically, where the parameter p21 (center wavelength 500 nm), p45 (center wavelength 620 nm) and p51 (center wavelength 650 nm) shown in Table 2 are selected as with the above, (−0.00119, 0.002346, 0.0016) of p21, (0.004022, 0.000068, −0.00097) of p45 and (0.005152, −0.00192, 0.000088) of p51 may be substituted as coefficients ($k_{pr}$, $k_{pg}$ and $k_{pb}$).

The embodiment 2 is constituted as described above. When any one of the scopes 10A to 10C shown in FIG. 4 is connected to the processor unit 42, the microcomputer 35 of the processor unit 42 makes communications with the microcomputer (20) of the scopes 10A to 10C, thereby obtaining the identification information on the signal output mode of these scopes. When the selector 43 is changed on the basis of the information and the scope 10A is connected, a color space conversion processing circuit 44 is selected. In this instance, RGB matrix data Pd is read from the memory 36, and a spectral image is formed by λ1, λ2 and λ3 signals of three wavelength ranges (three-color mode) or of one wavelength range (monochrome mode) selected by the matrix data Pd and RGB signals.

On the other hand, where the scope 10B or 10C, is connected, the selector 43 selects the color space conversion processing circuit 29. In this instance, Y/C matrix data Pc is read from the memory 36, and a spectral image is formed by λ1, λ2 and λ3 signals of three wavelength ranges or of one wavelength range selected by the matrix data Pc and Y/C signals. In such a manner, in the embodiment 2, any of the scopes 10A to 10C, different in output mode can be used by connecting to a single processor unit 42.

The endoscope apparatus according to Embodiment 2 may be constituted so that the identification information on signal output mode of the scopes 10A, 10B and 10C is recognized by analyzing image signals obtained by the CCD 15 through 15C or judging identification forming components, etc., arranged in the connector connection part in connection not by communications with microcomputers.

Further, in the endoscope apparatus, there is a case where both Y/C signals and RGB signals are formed by a single processor unit depending on the constitution of signal processing circuits such as DSP inside the processor unit. In this case, the Y/C spectral image forming circuit and the RGB spectral image forming circuit are selectively used to form and display a spectral image of the either circuit by utilizing Y/C signals and RGB signals as in the case according to Embodiment 2.

Since the endoscope apparatus of the present invention is able to form a spectral image directly from Y/C signals, it is advantageous in that circuits can be configured simply. Further, according to the second and third aspects of the invention, a spectral image can be obtained either from Y/C signals or RGB signals, and an endoscope different in a signal outputting mode can be connected for use, thereby providing a convenient endoscope apparatus.

The entire disclosure of each and every foreign patent application from which the benefit of foreign priority has been claimed in the present application is incorporated herein by reference, as if fully set forth.

What is claimed is:

1. An endoscope apparatus comprising:
    an endoscope comprising an imaging device that forms color image signals of a body to be observed;
    a Y/C signal processing circuit that forms brightness/color difference signals from a color image signal obtained by the imaging device;
    a first storage portion that stores Y/C matrix data for forming a spectral image based on the brightness/color difference signals; and
    a Y/C spectral image forming circuit that conducts matrix calculation by the Y/C matrix data of the storage portion and the brightness/color difference signals output from the Y/C signal processing circuit and forms a spectral image of an arbitrarily selected wavelength range.

2. An endoscope apparatus comprising:
    an endoscope comprising an imaging device that forms color image signals of a body to be observed;
    an image signal processing circuit comprising one of (i) a Y/C signal processing circuit that forms brightness/color difference signals from a color image signal obtained from the imaging device and (ii) an RGB signal processing circuit that forms RGB signals from a color image signal obtained from the imaging device;
    a first storage portion that stores Y/C matrix data for forming a spectral image based on the brightness/color difference signals;
    a Y/C spectral image forming circuit that conducts matrix calculation by the Y/C matrix data of the storage portion and the brightness/color difference signals output from the Y/C signal processing circuit and forms a spectral image of a first arbitrarily selected wavelength range;
    a second storage portion that stores RGB matrix data for forming a spectral image based on the RGB signals; and
    an RGB spectral image forming circuit that conducts matrix calculation by the RGB matrix data of the storage portion and the RGB signals output from the RGB signal processing circuit and forms a spectral image of a second arbitrarily selected wavelength range,
    wherein either the Y/C spectral image forming circuit or the RGB spectral image forming circuit can be selected.

3. The endoscope apparatus according to claim 2, which comprises a processor unit detachably connected to the endoscope,
    wherein the image signal processing circuit is disposed in the endoscope,
    both of the Y/C spectral image forming circuit and the RGB spectral image forming circuit are disposed in the processor unit, and
    in the processor unit, either the Y/C spectral image forming circuit or the RGB spectral image forming circuit is selected based on an identification information on the endoscope.

* * * * *